US00PP33497P2

(12) United States Plant Patent
Vicente

(10) Patent No.: US PP33,497 P2
(45) Date of Patent: Sep. 21, 2021

(54) ***HYDRANGEA* PLANT NAMED 'HYD CELEST'**

(50) Latin Name: *Hydrangea macryophylla*
Varietal Denomination: HYD CELEST

(71) Applicant: Fresca Farms, Miami, FL (US)

(72) Inventor: Mario I Vicente, Miami, FL (US)

( * ) Notice: Subject to any disclaimer, the term of this patent is extended or adjusted under 35 U.S.C. 154(b) by 0 days.

(21) Appl. No.: 17/093,918

(22) Filed: Nov. 10, 2020

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP20,140 P2 * 6/2009 Shiobara ..... A01H 5/02
Plt./250

OTHER PUBLICATIONS

Knox. French *Hydrangea* for Gardens in North and Central Florida. UF IFAS Extension ENH1069, 6 pp. (Year: 2017).*

* cited by examiner

*Primary Examiner* — June Hwu
(74) *Attorney, Agent, or Firm* — Mariana Vernieri

(57) ABSTRACT

A new and distinct cultivar of *Hydrangea* plant named 'HYD CELEST', characterized by its upright habit; strong roots and stems; large dark green-colored leaves; and large mophead-type inflorescences with bi-colored flowers of irregular patterns, and an increased resistance to powdery mildew.

7 Drawing Sheets

Botanical designation: *Hydrangea macryophylla.*
Family—Hydrangeaceae.
Scientific name—*Hydrangea macrophylla* (Thunb.) Ser.
Cultivar denomination: 'HYD CELEST'.

BACKGROUND OF THE INVENTION

The present invention relates to a new and distinct variety of *Hydrangea macrophylla* (Thunb.) Ser. that is grown for use as an indoor floral potted plant and an outdoor ornamental flowering shrub. The new cultivar is known botanically as *Hydrangea macrophylla* and will be referred to hereinafter by the cultivar name 'HYD CELEST'.

'HYD CELEST' resulted from asexual reproduction, through semi-hardwood cuttings, carried out by the inventor in Rionegro, Colombia with a range of day and night temperatures of 16° C. to 20° C. The purpose of the investigation that lead to this invention was to obtain a new variety of floral *Hydrangea* with unique flower colors, and, in particular, to obtain flowers displaying patterns of two distinct colors.

The inventor considers that 'HYD CELEST' is distinct from other varieties of *Hydrangea* known to the inventor in the following respects:

First, whereas other varieties of *Hydrangea* in commerce have flowers in a single color, 'HYD CELEST' flowers have two colors in the same petal, creating a hi-colored flower appearance.

Second, 'HYD CELEST' has an increased resistance to powdery mildew, when compared to all other varieties of *Hydrangea* known to the inventor. Powdery mildew s a fungal disease that affects a wide range of plants, and very typically forun in *Hydrangea*. Powdery mildew diseases are caused by many different species of fungi in the order *Erysiphales*, with *Podosphaera xanthii* being the most commonly reported cause. With a better resistance to this deseace, 'HYD CELEST' has its distinct benefits even beyond the novel color patterns in the petals of the flowers.

'HYD CELEST' was created as a result of cross-pollination, with the parentals being the 'White' (male parent) and 'Bogotana Blue' (female parent) colorations of *Hydrangea macrophylla*, repeatedly carried out by the inventor with the main purpose of diversifying the flower colors of the *Hydrangea* in a development program that lasted five years. During this program, by trial and error, those cuttings displaying the desired changes were selected, and asexually reproduced for five generations until obtaining the desired results. The method used for asexual propagation was softwood cuttings. The characteristics of the new *Hydrangea* cultivar named 'HYD CELEST' have been determined stable and are reproduced true to type in successive generations.

SUMMARY OF THE INVENTION

The following traits have been repeatedly observed and represent the characteristics of the new *Hydrangea* cultivar 'HYD CELEST'. These traits in combination distinguish 'HYD CELEST' from all other commercial varieties of *Hydrangea* known to the inventor. 'HYD CELEST' has not been tested under all possible conditions and phenotypic differences may be observed with variations in environmental, climatic and cultural conditions, without however, any difference in, genotype. Observations and dissections of the vegetative and reproductive parts of the plant were carried out with the help of a stereoscope. Color references were taken from The R.H.S. Colour Chart of The Royal Horticultural Society of London (R.H.S.), 6th edition (2015).

The new variety is distinguished from its parents in that the petals have two colors: white and blue; some petals have a white background with blue dots (spots) and the stem has fewer circular spots than the blue variety and it is more resistant to powdery mildew than the white variety. Additionally, if compared to plants of cultivar 'Dancing Angel' disclosed in U.S. Plant Pat. No. 20,140 and plants of French *Hydrangea*, the new variety of *Hydrangea* differs from 'Dancing Angel' in the petiole length and flower color; given that the 'Dancing Angel' has petioles of 1.8 cm and the flowers has petal close to 63A color becoming closer to 65C with development. On the other hand, the new *Hydrangea* differs to French *Hydrangea* mainly in the flower color, because the French *Hydrangea* has dark pink, pink, purple or blue flowers without spots. Flowering begins in week 20 and reaches its maximum opening in week 33. From this point on, the flower begins a natural aging process and can last on the plant until week 50. The plant's resistance to extreme hot/cold conditions has not been tested. Regarding the blue coloration, the pH plays an important role. If the soil conditions in the region are acidic, there is no need to add aluminum sulfate. There are trials of this new variety planted in neutral pH and indeed the color changed to pink, but it retained the characteristic spots of the variety.

1. *Hydrangea* 'HYD CELEST' is grown for use as both an indoor floral potted plant and an outdoor ornamental flowering shrub.
2. *Hydrangea* 'HYD CELEST' exhibits individual flowers that have bi-colored flowers in irregular patterns.
3. *Hydrangea* 'HYD CELEST' exhibits unique inflorescence development that produces an average of 500 sterile flowers and 50 smaller fertile flowers per inflorescence.
4. *Hydrangea* 'HYD CELEST' exhibits an upright habit.
5. *Hydrangea* 'HYD CELEST' is 43 cm in height and 34 cm. in diameter in a 1.5-liter container.
6. *Hydrangea* 'HYD CELEST' is a shrub.
7. *Hydrangea* 'HYD CELEST' is deciduous.
8. *Hydrangea* 'HYD CELEST' is asexually propagated by the method of semi-hardwood cuttings.
9. *Hydrangea* 'HYD CELEST' is more resistant to Powdery Mildew than all other commercial varieties of *Hydrangea* known to the inventor.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea*.

Figure 1:
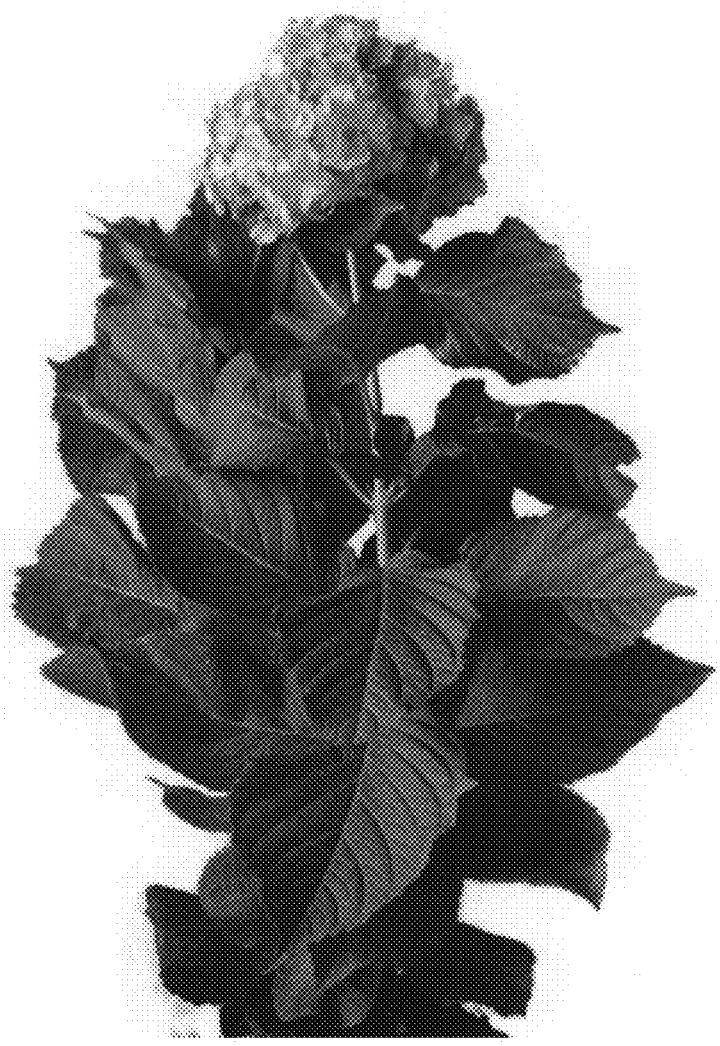
FIG. 1 depicts the growth habit of a specimen of the new variety of *H. macrophylla*, 'HYD CELEST' (age 32 weeks)
Figure 2:
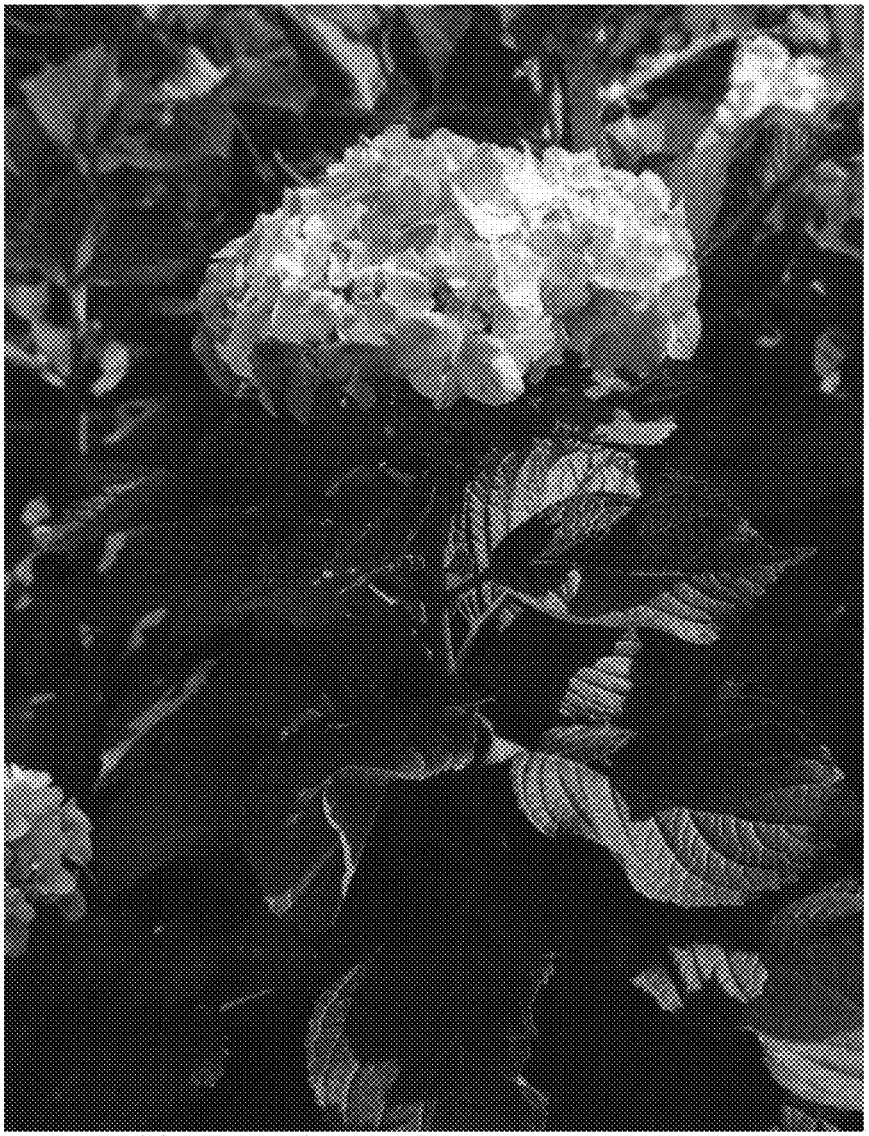
FIG. 2 illustrates a specimen of the 'HYD CELEST' in the field (age 30 weeks).
Figure 3:
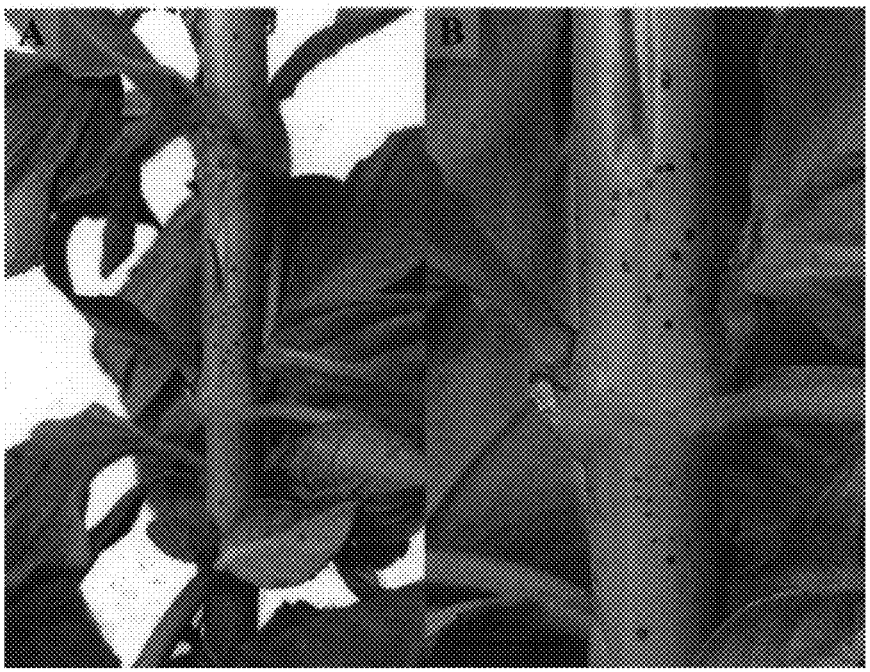
FIG. 3 shows the trunks and internodes of a 'HYD CELEST' plant, where part A shows a lateral view of the trunks and internodes and part B displays a close-up of lenticels on the internode.
Figure 4:
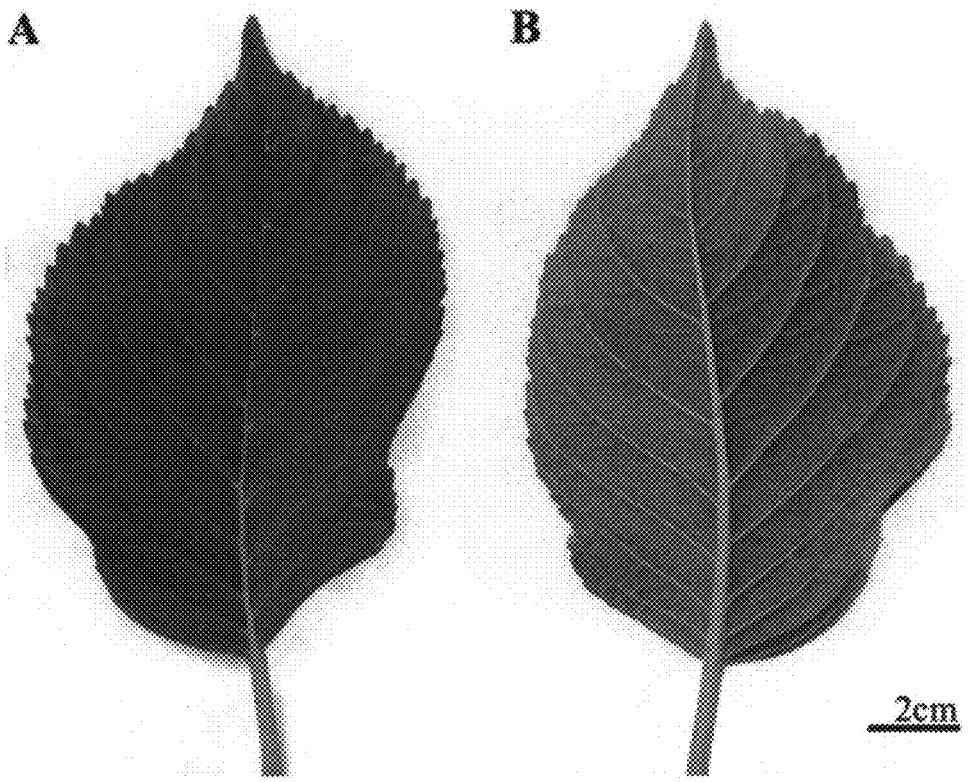

FIG. 4 features the leaves of a 'HYD CELEST', being part A the Upper Surface of the leaf and part B the Lower Surface of the leaf.

Figure 5:
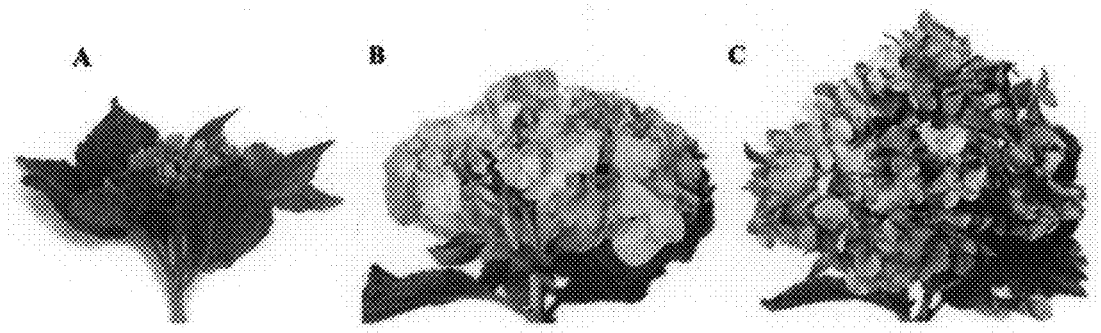

FIG. 5 illustrates the three development stages of the inflorescence of a 'HYD CELEST' plant. Part A shows the Bud stage (age 22 weeks), part B the blooming stage (age 30 weeks) and part C the Senescence stage (age 46 weeks).

Figure 6:
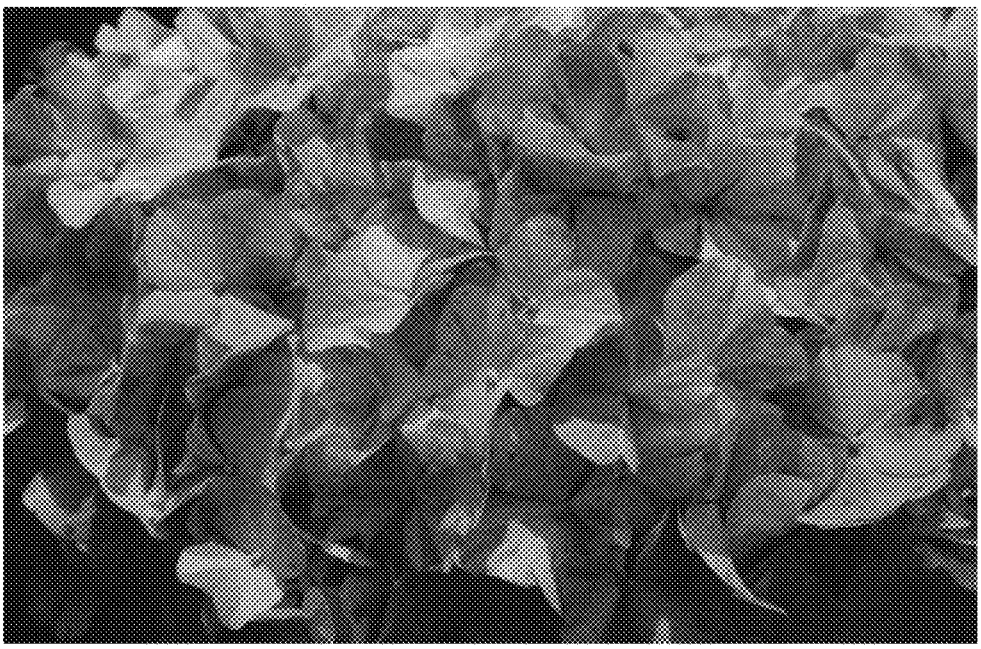

FIG. 6 is a General view of sterile flowers of the 'HYD CELEST' plant (age 32 weeks).

Figure 7:
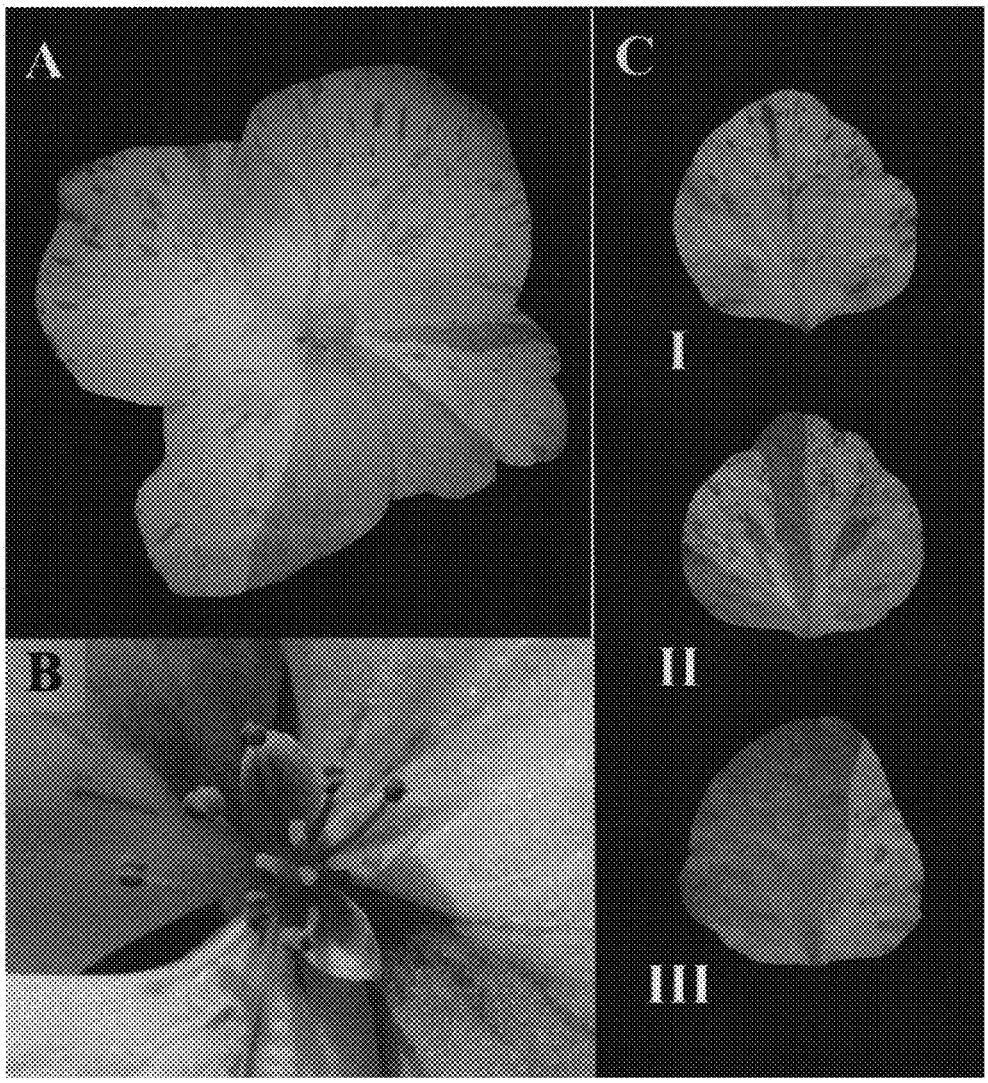

FIG. 7 is a close-up of sterile flowers of a 'HYD CELEST', where part A is an upper view of a sterile flower (age 34 weeks), part B is a Close-up of a sterile flower in anthesis (age 36 weeks), and part C shows the different types of coloration patterns in sepals of sterile flowers, these being Type I, white background with light blue spots, irregular spots with 0.5-1.0 mm diameter. Type II, Half light blue background, half white background with light blue spots, irregular spots with 0.5-1.0 mm diameter. Type III, White background with light blue stripes from from base to apex. Stripes with 3.0-4.0 mm width.

Figure 8:
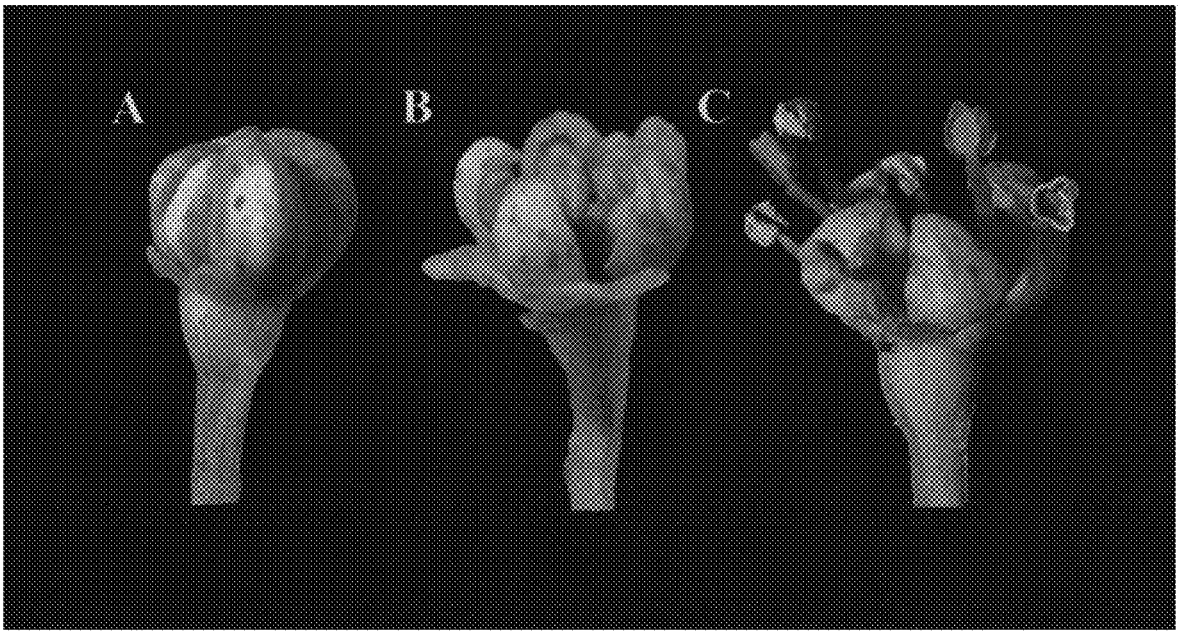

FIG. 8 shows the stages of anthesis of a fertile flower of a 'HYD CELEST' plant, where part A (age 33 weeks) and part B (age 35 weeks) show the pre-anthesis stage, and part C (age 37 weeks) shows the Anthesis stage.

BOTANICAL DESCRIPTION OF THE PLANT

The following is the detailed description of 'HYD CELEST'. The data which define these characteristics were collected from cultivated population obtained from asexual reproduction carried out in Rionegro, Colombia with a range of day and night temperatures of 16° C. to 20° C. Observations and dissections of the vegetative and reproductive parts of the plant were carried out with the help of a stereoscope. Color references were taken from The R.H.S. Colour Chart of The Royal Horticultural Society of London (R.H.S.), 6th edition (2015).

The methodology for processing the pollen grains was the KOH technique (Faegri & Iversen's technique modification). The description of the pollen grains was made based on the terminology of the book Illustrated Pollen Terminology, $2^{nd}$ edition (2018).

Root, stem, petiole and leaf portions were collected for analysis. The portions were fixed with FAA (10% of 40% formaldehyde, 50% of 96% ethanol, 5% of 96% acetic acid, and 35% of distilled water). Cross sections of each structure were obtained by free-hand slicing. Sections were stained with toluidine blue 0.05% and observed with a Leica DM500 optical microscope with 4× and 10× magnification. The characters analyzed describe the epidermis, the vascular system in general, xylem vessels and the cortex in each structure (Carlquist, 2013).

DESCRIPTION OF THE PLANT

Taxonomic classification:

*Family*.—Hydrangeaceae.

*Scientific name*.—*Hydrangea macrophylla* (Thunb.) Ser.

*Common name*.—Hortensia (spanish).

Plant:

*Growth habit*.—Upright.

*Stem strength*.—Strong (strong enough to hold one inflorescence).

*Branching habit*.—Non-branching (at first blooming). Branching after blooming.

*Plant height* (*from ground surface to foliage*).—40.0-47.0 cm.
*Plant height* (*from ground surface to flowers*).—49.0-58.0 cm.
*Plant diameter.*—32.0-36.0 cm.

Trunk:
*Main trunk length.*—40.0-47.0 cm.
*Main trunk diameter.*—0.8-1.2 cm.
*Trunk transversal section.*—Circular, no stem fasciation.
*Trunk color.*—Immature trunk color, light green RHS 143C to RHS 144A; Mature trunk color, dark green RHS 141A to RHS 141B.
*Trunk texture.*—Smooth.
*Trunk pubescence presence.*—Glabrous.
*Lenticel color.*—Dark brown RHS 187A, gray brown RHS 199B and dark blue RHS 103A.
*Lenticel diameter.*—0.5-1.1 mm.
*Internode length.*—3.1-5.9 cm.

Lateral branches:
*Number of lateral branches per plant.*—Two non-fully developed branches.
*Branch length.*—10.5-12.0 cm.
*Branch diameter.*—0.5 cm.
*Branch transversal section form.*—Circular.
*Branch angle.*—60° to 80°.
*Branch color.*—Immature branch color, light green RHS 143C to RHS 144A; Mature branch color, dark green RHS 141A to RHS 141C.
*Branch texture.*—Smooth.
*Branch pubescence.*—Glabrous.

Foliage:

General:
*Arrangement.*—Opposite decussate to sub-opposite.
*Number of leaves in the main trunk.*—Approx. 10 leaves.

Leaves:
*Leaf shape.*—Elliptic.
*Leaf apex shape.*—Acuminate.
*Leaf base shape.*—Rounded to oblique.
*Leaf margin shape.*—Ascending angular teeth with angular sinus.
*Leaf length.*—15.0-17.0 cm.
*Leaf width.*—10.0-13.0 cm.
*Leaf texture.*—Rough.
*Upper surface color.*—A color that varies between the color designations Green RHS 143A and RHS 143C.
*Lower surface color.*—A color that varies between the color designations Green RHS 139D and RHS 143D.
*Venation pattern.*—Pinnate.
*Venation color.*—Light green RHS 145A.

Petioles:
*Petiole length.*—3.0-4.0 cm.
*Petiole diameter.*—0.4 cm.
*Petiole transverse section from.*—Semicircular.
*Petiole color.*—Green RHS 143C.

Inflorescences:

Buds:
*Shape of cluster.*—Rounded.
*Number of buds per cluster.*—110-120.
*Cluster length.*—1.7 cm.
*Cluster width.*—1.8 cm.

Inflorescence:
*Inflorescence type.*—Terminal compound cymose panicle of both fertile flowers and sterile flowers comprising several clusters having one fertile flower per cluster, surrounded by several sterile flowers.
*Inflorescence form.*—Mophead.
*Inflorescence length.*—10.0 cm.
*Inflorescence diameter.*—16.0-18.0 cm.
*Average number of inflorescence per plant.*—One inflorescence until harvest.
*Average number of flowers per inflorescence.*—513-552 flowers.
*Average number of sterile flowers per inflorescence.*—458-505 sterile flowers.
*Average number of fertile flowers per inflorescence.*—47-55 fertile flowers.

Sterile flowers:

General description:
*Flower form.*—Cruciform.
*Flower diameter.*—24.9-34.8 mm.
*Flower depth.*—2.1-3.0 mm.

Petals:
*Number of petals per flower.*—4 petals.
*Petal shape.*—Elliptic and concave.
*Petal length.*—2.2-2.5 mm.
*Petal width.*—1.3-1.7 mm.
*Petal apex shape.*—Acute.
*Petal base shape.*—Cuneate.
*Petal margin shape.*—Entire.
*Petal color pattern.*—White background with light blue spots, irregular spots with 0.5-1.0 mm diameter.
*Petal upper and lower surface color.*—Mature petals with spots with light violet blue RHS 97B, RHS 97C, blue RHS 101C and light blue RHS 106C, background with light gray green RHS 196D, gray RHS N155A and white RHS N155B.
*Petal texture.*—Bumpy surface.

Sepals:
*Number of sepals per flower.*—4 sepals.
*Sepal shape.*—Ovate.
*Sepal length.*—12.6-17.5 mm.
*Sepal width.*—14.8-21.4 mm.
*Sepal apex shape.*—Rounded to indented, sometimes 2-lobed and irregular.
*Sepal base shape.*—Attenuate to cuneate.
*Sepal margin shape.*—Entire.
*Sepal color pattern.*—Type I, white background with light blue spots, irregular spots with 0.5-1.0 mm diameter. Type II, Half light blue background, half white background with light blue spots, irregular spots with 0.5-1.0 mm diameter. Type III, White background with light blue stripes from from base to apex. Stripes with 3.0-4.0 mm width.
*Sepal upper and lower surface color.*—Immature sepal, light green RHS 149A to RHS 149D; mature sepal with spots and stripes with light violet blue RHS 97B, RHS 97C, RHS blue 101C and light blue RHS 106C, background with light gray green RHS 196D, RHS gray N155A and white RHS N155B; sepals in senescence with spots and stripes with RHS violet 84A to RHS 84B, background with light green RHS 149B, RHS 149D and RHS yellow green 150A.
*Sepal texture.*—Bumpy surface.

Pedicels:
*Pedicel length.*—12.5-25.4 mm.
*Pedicel diameter.*—1.1-1.4 mm.
*Pedicel angle.*—45°-60°.
*Pedicel pubescence.*—Glabrous.

*Pedicel color pattern*.—White background with light blue spots. irregular spots with 0.5-1.0 mm diameter.
*Pedicel surface color*.—Pedicels with spots with light violet blue RHS 97B, RHS 97C, blue RHS 101C and light blue RHS 106C, background with light gray green RHS 196D, RHS gray N155A and white RHS N155B.

Stamens:
*Number of stamens per flower*.—6-8 stamens.
*Filament length*.—1.5-2.0 mm.
*Filament color*.—Blue RHS 101C and light blue RHS 106C.
*Anther shape*.—Longitudinal dehiscence, dorsifixed attachment.
*Anther length*.—0.2-0.9 mm.
*Anther color*.—Blue RHS 101C and light blue RHS 106C.

Pistil:
*Pistil number*.—1.
*Pistil length*.—1.1 mm.
*Style length*.—0.3 mm.
*Style color*.—Blue RHS 106A and green blue RHS 113C.
*Stigma number*.—2-4 stigmas.
*Stigma shape*.—Stigma surface linear long and narrow.
*Stigma color*.—Blue 105D.
*Ovary position*.—Ovary Superior.
*Ovary length*.—0.7 mm.
*Ovary width*.—0.6 mm.

Fertile flowers:
General description:
*Flower form*.—Cruciform.
*Flower diameter*.—2.2-3.3 mm.
*Flower depth*.—2.6-3.4 mm.

Petals:
*Number of petals per flower*.—4-5 petals.
*Petal shape*.—Elliptic and concave.
*Petal length*.—2.2-2.5 mm.
*Petal width*.—1.3-1.7 mm.
*Petal apex shape*.—Acute.
*Petal base shape*.—Cuneate.
*Petal margin shape*.—Entire.
*Petal color pattern*.—White background with light blue spots, irregular spots with 0.5-1.0 mm diameter.
*Petal upper and lower surface color*.—Mature petals with spots with light violet blue RHS 97B, RHS 97C, blue RHS 101C and light blue RHS 106C, background with light gray green RHS 196D, gray RHS N155A and white RHS N155B.
*Petal texture*.—Bumpy surface.

Sepals:
*Number of sepals per flower*.—5 sepals.
*Sepal shape*.—Ovate to elliptic
*Sepal length*.—0.5-2.0 mm.
*Sepal width*.—0.5-1.2 mm.
*Sepal apex shape*.—Acute — two lobed.
*Sepal base shape*.—Cuneate.
*Sepal margin shape*.—Entire.
*Sepal upper and lower surface color*.—Mature sepal light green RHS 145C and RHS N144A.
*Sepal texture*.—Smooth.

Pedicels:
*Pedicel length*.—3.4-5.0 mm.
*Pedicel diameter*.—0.8-1.0 mm.
*Pedicel angle*.—0°.
*Pedicel pubescence length*.—Minute pubescent (<0.125 mm).
*Pubescence density*.—Sparsely pubescent.
*Pedicel color pattern*.—White background with light blue spots, irregular spots with 0.5-1.0 mm diameter.
*Pedicel surface color*.—Pedicels with spots with light violet blue RHS 97B, RHS 97C, blue RHS 101C and light blue RHS 106C, background with gray RHS N155A and white RHS N155B.

Stamens:
*Number of stamens per flower*.—6-8 stamens.
*Filament length*.—1.4-2.0 mm.
*Filament color*.—Blue RHS 101C and light blue RHS 106C.
*Anther shape*.—Longitudinal dehiscence, dorsifixed attachment.
*Anther length*.—0.2-0.9 mm.
*Anther color*.—Blue RHS 101C and light blue RHS 106C.

Pistil:
*Pistil number*.—One pistil.
*Pistil length*.—2.1-2.5 mm.
*Style length*.—0.5-0.7 mm.
*Style color*.—Blue RHS 106A and green blue RHS 113C.
*Stigma number*.—3-4 stigmas.
*Stigma shape*.—Stigma surface linear long and narrow.
*Stigma color*.—Blue 105D.
*Ovary position*.—Ovary superior.
*Ovary length*.—0.4-0.5 mm.
*Ovary width*.—1.3-1.4 mm.

Pollen:
*Unit*.—Monad.
*Size*.—Small (5-20 μm).
*Symmetry*.—Radial.
*Polarity*.—Isopolar.
*Ambit*.—Circular to lobate.
*Shape*.—Oblate-spheroidal.
*Aperture*.—Colpus.
*Aperture number*.—3.
*Tectum*.—Present with columellae.
*Ornamentation*.—Reticulate.
*Exine length*.—1.88 μm.
*Sexina length*.—1.050 μm.
*Nexina length*.—0.823 μm.
*Equatorial eje length*.—19.92 μm (20.18) 20.44 μm.
*Polar eje length*.—19.97 μm (19.87) 19.76 μm.

Anatomy:
Root anatomy:
*Pattern primary xylem*.—Semi-polyarch.
*Epidermis*.—Uniseriate.
*Epidermis cells shape*.—Cuboid.
*Cortex cell composition*.—Parenchyma cells.
*Cortex thickness*.—0.29-0.35 mm.
*Vessel grouping*.—Solitary.
*Number of vessels per group*.—One vessel.
*Vessel element diameter*.—0.01-0.05 mm.
*Vessel density*.—14-19 vessels per mm2.

Trunk anatomy:
*Epidermis*.—Biseriate.
*Epidermis cells shape*.—Cuboid.
*Epidermis thickness*.—0.01-0.13 mm.
*Cortex cell composition*.—Parenchyma cells.
*Cortex thickness*.—1.13-1.62 mm.

*Vascular bundles*.—Open collateral bundle surrounded by photosynthetic cells.
*Photosynthetic cells pattern*.—Cells in abaxial arrangement and inter-vessels.
*Vessel grouping*.—Vessels in radial multiples.
*Number of vessels per group*.—2-3 vessels.
*Vessel element diameter*.—0.01-0.05 mm.
*Vessel arrangement*.—Diagonal and/or radial pattern.
*Vessel density*.—115-124 vessels per mm2.
*Xylem porosity*.—Vessels with more or less the same diameter throughout the growth ring.
*Growth ring types*.—7B diffuse-porous.
*Imperforate elements*.—Fibre-tracheitis.
*Sieve-tube elements distribution*.—Tangential bands.

Petiole anatomy:
*Type of bundles*.—Colateral.
*Petiole vascular pattern*.—Bundles free to slightly fused.
*Traces*.—Free traces in a ring with medullary bundles.
*Branching of traces*.—Unbranched.
*Retitucation of traces*.—Unequally.
*Number of traces*.—6-7 traces.
*Vessel element diameter*.—0.02-0.04 mm.
*Vessel density*.—120-138 vessels per mm2.

Leaf anatomy:
*Upper epidermis*.—Uniseriate.
*Shape of the cells of the upper epidermis*.—Cuboid to slightly tabular.
*Type of palisade mesophyll*.—Biseriate.
*Lower epidermis*.—Uniseriate.
*Shape of the cells of the lower epidermis*.—Cuboid to slightly tabular.
*Type of vascular bundle*.—Collateral.
*Vascular pattern of midrib*.—Bundles fuse and form a flat arc with dorsal free traces.
*Number of traces*.—3-4 traces.
*Cellular composition of the midrib*.—7-8 layers of parenchyma cells surround the vascular bundle, in which there are conspicuous rays. Followed by the parenchyma, in an abaxial arrangement with respect to the vascular bundle, there are 3 to 4 layers of collenchymal cells.
*Type of thickness of collenchyma cells wall*.—Angular.

The invention claimed is:

1. A new and distinct *Hydrangea* plant named 'HYD CELEST' as illustrated and described herein.

* * * * *